United States Patent [19]

Dorman et al.

[11] Patent Number: 4,772,263
[45] Date of Patent: Sep. 20, 1988

[54] SPRING DRIVEN INFUSION PUMP
[75] Inventors: Frank D. Dorman; Henry Buchwald, both of Minneapolis, Minn.
[73] Assignee: Regents of the University of Minnesota, St. Paul, Minn.
[21] Appl. No.: 102,778
[22] Filed: Sep. 23, 1987

Related U.S. Application Data

[63] Continuation of Ser. No. 825,197, Feb. 3, 1986, abandoned.

[51] Int. Cl.⁴ .................... A61M 5/20; A61M 1/00
[52] U.S. Cl. ................... 604/132; 604/891.1; 604/134; 128/DIG. 12
[58] Field of Search ................ 604/131–132, 604/134, 138, 151, 153, 891.1

[56] References Cited

U.S. PATENT DOCUMENTS

| 2,815,152 | 12/1957 | Mills . | |
|---|---|---|---|
| 2,947,470 | 8/1960 | Ruben et al. | 604/134 |
| 3,023,750 | 3/1962 | Baron . | |
| 3,731,681 | 5/1973 | Blackshear et al. . | |
| 3,951,147 | 4/1976 | Tucker et al. | 604/891 |
| 4,056,095 | 11/1977 | Rey et al. | 604/891 |
| 4,299,220 | 11/1981 | Dorman . | |
| 4,373,527 | 2/1983 | Fischell . | |
| 4,447,224 | 5/1984 | DeCant, Jr. et al. . | |
| 4,487,603 | 12/1984 | Harris | 604/891 |
| 4,557,726 | 12/1985 | Reinicke . | |
| 4,718,893 | 1/1988 | Dorman et al. | 604/891.1 |

OTHER PUBLICATIONS

PCT Application No. PCT/US80/00176.
Implantable Infusion Pumps, Buchwald and Rohde, Department of Surgery, University of Minnesota, ©1984, Year Book Medical Publishers, Inc., pp. 177–221.
Implantable Drug Infusion Devices, Surgical Rounds, Buchwald and Rohde, Department of Surgery, University of Minnesota, Jul. 1984, pp. 16–23.
Selected pages from a thesis entitled, "A Methodical Design Study of Miniature Perfusion Devices for Chemotherapy of Cancer of the Head and Neck", Soden, Department of Mechanical Engineering, Manchester College of Science and Technology, Oct. 1965, pp. 165–166 and 229–231, and FIGS. 77(a) and 77(b).
II: The Design of Flat Diaphragms, Chapter 18 entitled, "Convex Diaphragms–Snap Action, pp. 201–206.
Mechanical Springs, Chapter XIV entitled, "Initially Coned Disk (Belleville) Springs, pp. 238–262.

Primary Examiner—C. Fred Rosenbaum
Assistant Examiner—Gene B. Kartchner
Attorney, Agent, or Firm—Merchant, Gould, Smith, Edell, Welter & Schmidt

[57] ABSTRACT

An implantable infusion pump (20) for infusing drugs or other chemicals or solutions into the body. A flexible spring diaphragm (25) forms an outer back wall portion (26) of a housing (22) of the infusion pump (20). The spring diaphragm (25) applies substantially constant force over a range of displacement and communicating internal body pressure to the drug chamber (30) so as to maintain a substantially uniform pressure difference between the drug chamber (30) and the internal body pressure.

15 Claims, 2 Drawing Sheets

SPRING DRIVEN INFUSION PUMP

This is a continuation, of application Ser. No. 825,197, filed Feb. 3, 1986 now abandoned.

BACKGROUND OF THE INVENTION

The present invention relates to an implantable infusion pump for infusing drugs or other chemicals or solutions into a body wherein the infusion pump is implanted. More particularly, the present invention relates to an implantable infusion pump which compensates for changes in ambient pressure and is largely unaffected by changes in ambient temperature so as to accurately control the flow rate of drugs from the implantable infusion pump into the body.

Infusion pump designs were rarely seen in medical literature until the 1950s. Most of these early infusion pumps were extracorporeal devices of various designs. One such device included a reciprocating air pump driven by an electric motor. Yet another design considered comprised a metal housing for a glass syringe and a compression chamber fed by a tank of nitrogen gas. Yet another such infusion pump included a motorized syringe pump which included an electric motor connected to the worm drive that moved a syringe plunger by a gear box. The gears were interchangeable such that replacement of the gears permitted different delivery rates. Yet another infusion pump included a syringe plunger driven by a rider on a threaded shaft. Numerous other designs were considered for these extracorporeal infusion pumps. P. D. W. Soden in his thesis entitled, "A Methodical Design Study of Miniature Profusion Devices For Chemotherapy of Cancer of the Head and Neck", studied possible designs for producing a miniature profusion device to be carried by ambulating patients receiving chemotherapeutic treatment for cancer of the head and neck. Quoting from his thesis, "Approximately two million alternative design solutions were synthesized and recorded in compact matrix form on a 'morphological chart'". One of the numerous design concepts mentioned by Soden for possible use with an extracorporeal infusion pump was the use of a small tubular arrangement containing an elastic metal bellows possibly constructed from preloaded disks so as to form a relatively small diaphragm in the tubular arrangement for exerting a fairly constant force on the drug solution being infused. Due to the size of the diaphragm, this design provided for very little, if any, compensation for changes in atmospheric pressure.

One of the earliest implantable infusion pumps intended for use in laboratory animals comprised a microinjector comprising a compressed spring held away from a rubber-capped glass tube by a metal alloy disk with a low melting point. Administration of the injection was accomplished by placing the animal near the coils of a high-frequency induction heater. Activation of the coils melted the alloy disk and the spring ejected infusate into the desired site in the animal. A second implantable infusion pump for the continuous infusion of drugs utilized the osmotic pressure developed by a saturated aqueous solution of Congo red dye against water as its power source. The infusion pump comprised a partially collapsed rubber compartment filled with Congo red dye separated from a second water compartment by a semi-permeable cellophane member. Expansion of the rubber compartment as the water moved by osmosis into the Congo red solution ejected the drug from the infusion pump.

Implantable infusion pumps were clinically introduced in 1975. Implantable infusion pumps currently in clinical use or in animal trials anticipating clinical studies in the near future, include vapor pressure powered pumps, peristaltic pumps, and pulsatile solenoid pumps. The vapor pressure powered pump was developed at the University of Minnesota and is described hereafter. The peristaltic pump generally comprises a flexible tube placed in a u-shaped chamber in contact with rollers that press against the tube with sufficient force to occlude the tube's lumen. The rollers are rotated by a motor. As the rotor turns and the rollers compress the lumen of the tube, fluid is moved toward an exit. The rollers and housing are arranged so that a second roller begins to squeeze the tube before the first disengages, preventing backflow of the infusate. Sandia Laboratories, Siemens AG, and Medtronic, Inc. have developed implantable pumps with peristaltic pumping mechanisms. A pulsatile solenoid pump includes a solenoid driven reciprocating chamber with two check valves to move infusate from the reservoir out through the delivery catheter. Infusate is stored in a flexible metal diaphragm reservoir. Such a pump has been developed by Fischell and colleagues at Johns Hopkins University Applied Physics Laboratory and by the Pacesetter Corporation.

These currently available implantable infusion pumps provide drug infusion into the body at rates which are more precisely controllable than can be achieved by conventional oral and bolus injection methods. However, the existing implantable infusion pumps are sensitive to temperature and atmospheric pressure changes such that changes in temperature and atmospheric pressure cause corresponding changes in drug infusion rates from the implantable infusion pumps into the body. With some drugs, particularly those having small therapeutic indices, such changes in drug infusion rates are undesirable and, in certain situations, unacceptable.

One example of an existing implantable infusion pump is described in U.S. Pat. No. 3,731,681, herein incorporated by reference, which describes an implantable infusion pump which uses a liquid/vapor equilibrium to maintain a constant pressure on a drug solution, such as insulin, contained in a drug chamber of the infusion pump in order to maintain a predetermined flow rate of the drug solution from the drug chamber via a capillary tube to an infusion site in the body. In the liquid/vapor powered pump, double chambered design with a rigid outer chamber and a flexible diaphragm separating the chambers is utilized. A liquid/vapor is present in one of the chambers either as a power source or to allow the diaphragm to move without creating a vacuum. However, due to the rigid outer shell structure of the pump, this technique of drug flow control is affected by changes in temperature and atmospheric pressure. Where the patient remains in a local region, the air pressure is a minor variable. However, there are conditions under which both temperature and pressure can change a significant amount. For example, if the patient has a fever, the temperature can change several degrees. The internal pressure change is about 0.5 psi per degree fahrenheit. Assuming an 8 psi driving force at 98.6° F., a twenty-five percent (25%) increase in pressure and drug flow rate can result from a fever of 102.6 degrees fahrenheit. Such changes in flow rate may be unacceptable for certain drugs with small therapeutic indices.

An even more serious situation results from changes in atmospheric pressure. Atmospheric pressure change at any given location on the earth does not significantly affect flow rate of this pump. However, with modern modes of transportation, a patient can rapidly change altitude during travel, such as when traveling in the mountains or when traveling by plane wherein cabin pressures equivalent to five thousand to six thousand feet of altitude are not uncommon. Since the vapor/pressure powered implantable infusion pump of U.S. Pat. No. 3,731,681 is enclosed in a rigid, immovable outer shell structure, it produces a constant internal pressure (at constant temperature) independent of the external pressure. The hydrostatic pressure within the body closely follows the external pressure on the body caused by atmospheric pressure. This is largely due to the compliance of the lungs and the venous circulation. The net effect is a pressure difference across the outflow resistance from the infusion pump (typically a capillary tube or the like) which changes linerally with external pressure. The drug flow rate can increase as much as forty percent (40%) when the patient takes a commercial airline trip.

One method of more accurately controlling the rate of drug delivery is an infusion regulator, such as that disclosed in U.S. Pat. No. 4,299,220. The infusion regulator described therein meters the rate of drug delivery on the basis of the pressure drop across the output or outflow resistance (capillary tube) using a diaphragm valve. An undesirable feature of the infusion regulator is that the drug solution flows through a metering valve at high local shear rates, which may be inappropriate for certain proteinaceous or micellar solutions.

The present invention overcomes these and other problems associated with currently available implantable infusion pumps and infusion regulators.

SUMMARY OF THE INVENTION

The present invention relates to an infusion pump for implantation in a living body. The infusion pump includes a housing having a drug chamber. The housing of the infusion pump includes a spring energy source means for forcing drug solution out of the drug chamber and compensating for changes in internal body pressure whereby pressure differential between the drug chamber and the internal body pressure remains constant, unaffected by changes in body temperature or atmospheric pressure. The housing further includes an inlet conduit in communication with the drug chamber and an outlet conduit in communication with the drug chamber which leads to an infusion site in the body. A self-sealing, penetrable member is provided in the inlet conduit and is unobstructed so that the infusion pump can be implanted in the body with the unobstructed, penetrable member situated such that the drug chamber can be periodically refilled with a drug solution by injection through the skin.

In the preferred embodiment, the spring energy source means includes spring diaphragm means forming a flexible, exterior backwall of the drug chamber for applying pressure on the drug solution in the drug chamber, equal to a predetermined constant force exerted by the spring diaphragm plus force exerted by the internal body pressure.

The spring diaphragm means in one embodiment of the present invention preferably includes a spring diaphragm which exerts substantially constant force over a predetermined range of movement. The spring diaphragm forms a movable, flexible outer wall portion of the housing and cooperates with rigid wall portions of the housing to form a variable volume drug chamber. The internal pressure of the drug chamber is generated by the external spring diaphragm which is exposed to the internal pressure of the body at the implantation site. When the pump is implanted in soft tissue where it is not compressed by bony or other rigid structures, the external pressure acting on the spring diaphragm will not depart appreciably from atmospheric pressure. The internal pressure of the drug chamber will thus vary with external pressure exerted on the spring diaphragm and the pressure difference across the outlet conduit (e.g., capillary flow restrictor) will be substantially constant and correspond to the force applied on the drug chamber by the spring diaphragm.

Because the infusion pump of the present invention compensates for changes in ambient pressure, such a pump will perform properly when driven by internal pressures lower than those used in the vapor/pressure powered pump previously discussed, which uses a pressure of 8–10 psi to minimize variation caused by temperature and atmospheric pressure changes. Reduction of this driving pressure in a vapor/pressure powered pump (e.g., by using a different gas) would increase error substantially. The spring driven infusion pump of the present invention can use a smaller operating pressure limited by different and smaller variables. The changes in external pressure on the pump and at the delivery site set a lower limit for the operating pressure of the present invention.

In the preferred embodiment of the present invention, the spring diaphragm forms a portion of the strong outer shell or housing of the infusion pump and is configured to provide a nearly constant force over the traveled distance corresponding to the infusion pump's drug delivery volume. Because of the relatively large area of the diaphragm, the force applied is large, thus requiring a relatively thick diaphragm. Constant force is obtained by using the snap action effect of conical washer springs. A plurality of conical spring sections are alternated radially with stronger reversed angle conical spring sections and/or substantially stiff cylindrical rings in order to make a substantially flat force/deflection curve. The proper thickness, cone angle, and material properties can be selected to give a constant force of a selected magnitude over a given distance, as illustrated in the force/deflection curve of FIG. 3. Conical spring sections of this type are frequently referred to as Belleville washers and at a height to thickness ratio of 1.5:1, an extended linear force region can be obtained.

In the preferred embodiment, the inner surface of the top wall portion of the housing is configured so as to nest with the spring diaphragm so as to enable most of the drug solution contained in the drug chamber to be expelled. In some embodiments, the inner surface of the top wall portion might also include a spring diaphragm means. However, the primary flex action will occur at the thinner spring diaphragm forming a part of the bottom wall portion of the infusion pump.

These and various other advantages and features of novelty which characterize the present invention are pointed out with particularity in the claims annexed hereto and forming a part hereof. However, for a better understanding of the invention, its advantages and objects attained by its use, reference should be had to the drawings which form a further part hereof and to the accompanying descriptive matter in which there is illustrated and described a preferred embodiment of the present invention.

BRIEF DESCRIPTION OF THE DRAWINGS

In the drawings, in which like reference numerals and letters indicate corresponding parts throughout the several views.

DETAILED DESCRIPTION OF A PREFERRED EMBODIMENT OF THE PRESENT INVENTION

Figure 1:
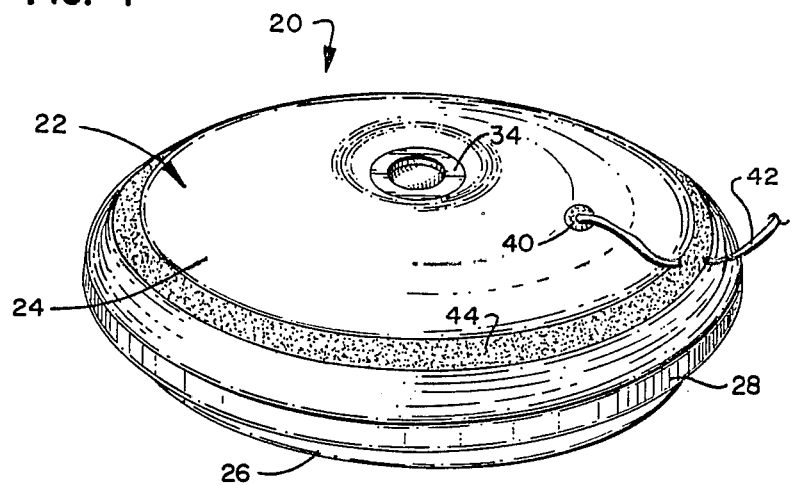
FIG. 1 is a view in perspective of an embodiment of an infusion pump in accordance with the principles of the present invention.
Figure 2:
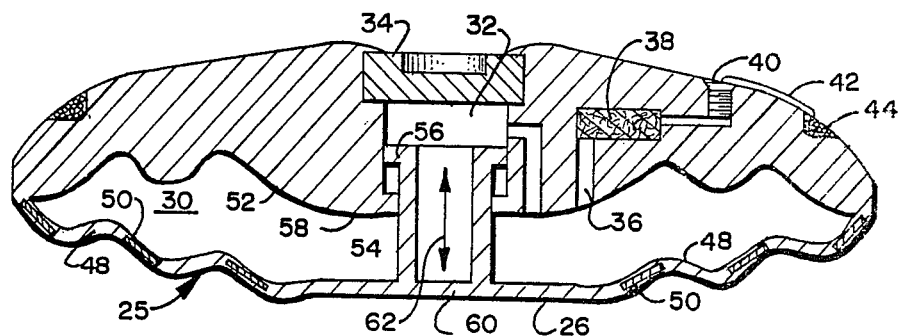
FIG. 2 is a sectional view of the embodiment shown in FIG. 1 with portions thereof being shown diagrammatically.

Referring now to the drawings, there is illustrated in FIGS. 1-2 a preferred embodiment of an implantable infusion pump in accordance with the principles of the present invention, the pump being generally designated by the reference numeral 20. The pump 20 has a housing 22 with top and bottom wall portions 24,26 interconnected by a side wall portion 28 forming a strong outer shell structure. (The expressions "top" and "bottom" are relative and refer only to positions that are generally shown in the drawings.) In the embodiment shown, the housing 22 has a generally cylindrical shape. The bottom wall portion 26 includes a flexible spring diaphragm 25 which cooperates with the remainder of the housing to define a variable volume, fluid-tight drug chamber 30 for holding a drug solution or other chemicals or solutions to be infused into an infusion site of a patient's body wherein the infusion pump is implanted.

As illustrated in FIGS. 1-2, the infusion pump 20 includes the standard features required of an implantable and refillable infusion pump. An inlet conduit 32 extends from the exterior of the housing 22 to the variable volume drug chamber 30 so as to provide for fluid communication from outside the housing 22 to the drug chamber 30. An upper end of the inlet conduit 32 includes a self-sealing, penetratable member or septum 34, suitably positioned therein in so as to provide a fluid type seal and yet provide for refilling of the drug chamber 30 by injection. An outlet conduit 36 leads from the drug chamber 30 to the exterior of the housing 22 so as to provide for outflow of drug solution from the drug chamber 30 to the exterior of the housing 22. The outlet conduit 36 is illustrated as including a suitable filter 38 for filtering out bacteria and trapped gas, which might be inadvertently introduced into the infusion pump 20 during the refilling process. Interconnected to an outer end of the outlet conduit 36 by a suitable connector 40 is capillary tubing 42 which serves as a flow regulating resistance element or flow restrictor. The capillary tubing 42 might be interconnected at an opposite end to a rubber catheter or the like that leads to the site of infusion in the body. Several feet of capillary tubing 42 is typically required (e.g., 50-100 feet).

The flow rate through the flow restrictor is governed by the Poisseuille equation as follows:

$Q = (\pi r D^4 \Delta P)/128 \mu L$, where $Q$=flow in ml/sec., $D$=diameter in cm., $\mu$=viscosity in poise, $\Delta P$=pressure in dynes/cm$^2$, and $L$=length in cm. The most readily adjustable parameters are the length and diameter of the capillary and the viscosity of the infusate. As illustrated, the capillary tubing 42 might be wrapped about the housing 22 in a groove 44 and suitably secured by a material compatible with body fluids. It will be appreciated that other types of devices might be used to provide for drug output or outflow resistance; for example, spiral groove plate, etched glass, steel capillary tubing, silica chip, etc. Moreover, the resistance elements may number more than one, as in the case of more than one site of infusion.

The outer surface of the top wall portion 24 of the housing 22 is preferably shaped to allow easy identification of the inlet conduit 32 and suitably protected with a layer of metal or the like to be protected from needle damage during the process of refilling the drug chamber 30. The bottom wall portion 26 and side wall portion 28 might also be similarly protected by a metal layer. It will be appreciated that the overall design of the infusion pump 20 of the present invention can be more compact and have higher volumetric efficiency than vapor/pressure powered pumps since there is no second chamber and the outer shell structure of the infusion pump serves a dual purpose as the spring diaphragm and protective shell.

As with currently available implantable infusion pumps, the infusion pump 20 of the present invention is constructed of materials non-toxic to the patient and compatible with both the drug solution and the body fluids. Titanium is a desirable material for forming a large portion of the housing 22, fittings, etc. All components of the infusion pump 20 will be made of materials compatible with body fluids and commonly used for construction of devices to be implanted within the body.

Figure 5:
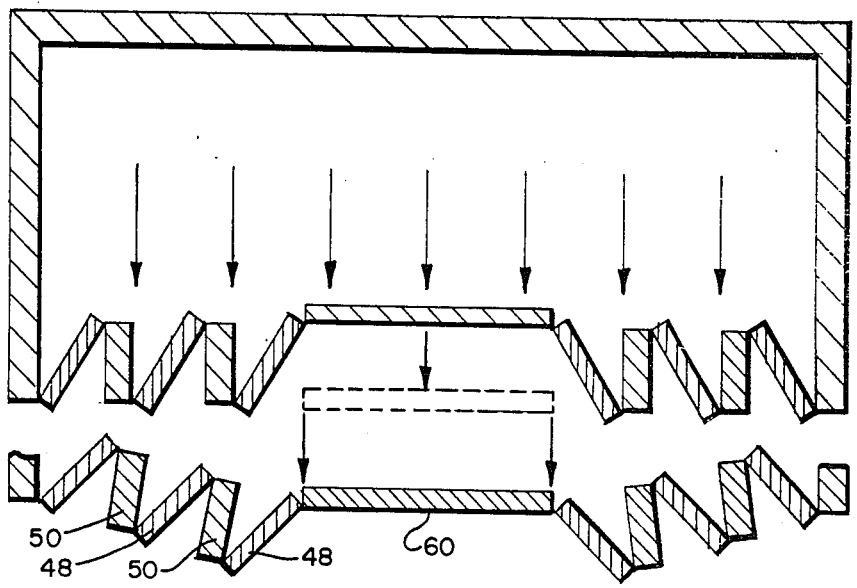
FIG. 5 is a diagrammatic view generally illustrating drug chamber pressure forces and movement of a flexible spring diaphragm into and out of a chamber generally in accordance with the principles of the present invention.

In the embodiment of the infusion pump shown in FIGS. 1-2, and as diagrammatically illustrated in FIG. 5, the spring diaphragm 25 includes a series of nested conical sections 48 interconnected by stiff cylindrical ring sections 50 so as to form a substantially flat spring diaphragm. The conical sections 48 are constructed of an elastomer with a low elastic constant, and the ring sections 50 are preferably constructed of metal with a high elastic constant. The preferred construction technique is to mold the metal ring sections 50 into an elastomer structure forming the conical sections 48. If necessary, the inner surface of the spring diaphragm 25 can be coated with a plastic liner to resist drug action on the elastomer and reduce gas diffusion from the body into the drug chamber 30. A thin metal diaphragm might be used as a liner if necessary, to better isolate the drug solution in the drug chamber 30 by resisting gas and liquid diffusion.

Figure 3:
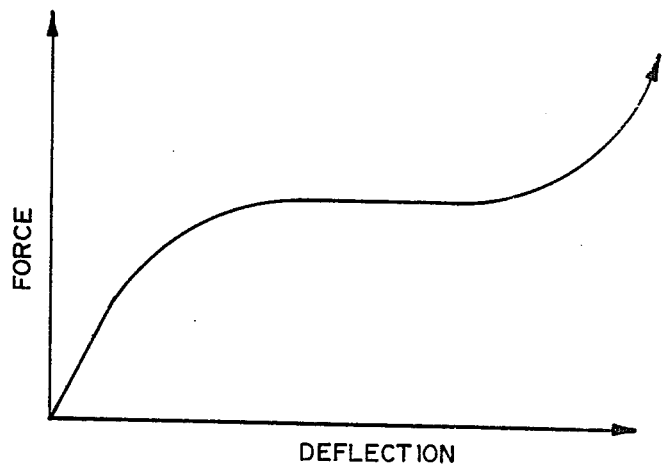
FIG. 3 is a force/deflection curve illustrating substantially constant force over a predetermined range of deflection or movement exemplary of a spring diaphragm such as might be utilized in an infusion pump in accordance with the principles of the present invention.
Figure 4:
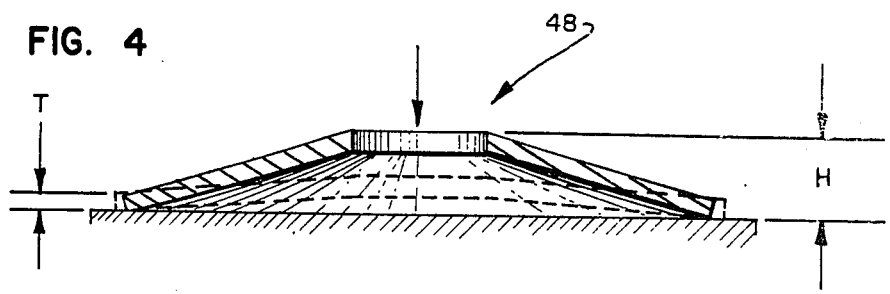
FIG. 4 is a sectional view of a single conical spring section.

The above described arrangement of conical sections 48 and ring sections 50 provide a spring diaphragm 25 with a longer useful range of movement or stroke than possible with a single conical spring section such as a single Belleville washer of the type that is generally shown in FIG. 4. However, a Belleville washer such as shown in FIG. 4 with the proper selection of cone angle and thickness can yield a force displacement curve as shown in FIG. 3. The flat portion of the curve is a constant force region that can be used to produce a constant pressure over some range of displacement volume. The curve in FIG. 3 is obtained when the ratio of of height H of the cone to thickness T is about 1.5:1. If a strong material like Titanium is used, cone height must be very small, i.e., 10 to 20 thousandths of an inch, so as to provide force in the range suitable for infusion pumps such as 4 to 15 psi. This range of heights, which constitutes the effective stroke of a spring diaphragm including a single conical spring, is too small to be practical for use in infusion pumps. In order to retain a flat pressure curve and achieve a longer stroke or range of movement of the spring diaphragm 25, a spring material with a lower elastic constant can be used; for example, plastics and elastomers. When low elastic materials are used, the thickness of the conical section can be increased and the cone angle made larger. This allows the spring diaphragm 25 to have a much longer range of travel in the substantially flat portion of the curve shown in FIG. 3. The spring material also should have a much greater percent elongation in the elastic region of its stress strain curve. By separating the single conical spring into a nested series of conical sections interconnected by relatively stiff cylindrical ring sections a substantially flat spring diaphragm having an effective stroke or range of movement in the substantially flat portion of the force/deflection curve shown in FIG. 3 which is required of infusion pumps is derived. Nesting of conical sections and movement of the spring diaphragm 25 is diagrammatically illustrated in FIG. 5. In typical applications, the spring diaphragm will have a range of movement of stroke of about 1 to 2 cm. It will be appreciated that the shape and thickness of the spring diaphragm 25 may vary in order to exhibit the required force/deflection characteristics.

The conical sections are preferably made of a high temperature aerospace plastic like polyamide (Torlon ®) or the aromatic polyester liquid crystal polymer (Xydor ®). These materials have a flexual modulus of about two million psi versus about ten to twelve million psi for metals. Moreover, these plastics are moldable to the thicknesses and shapes required.

Figure 6:
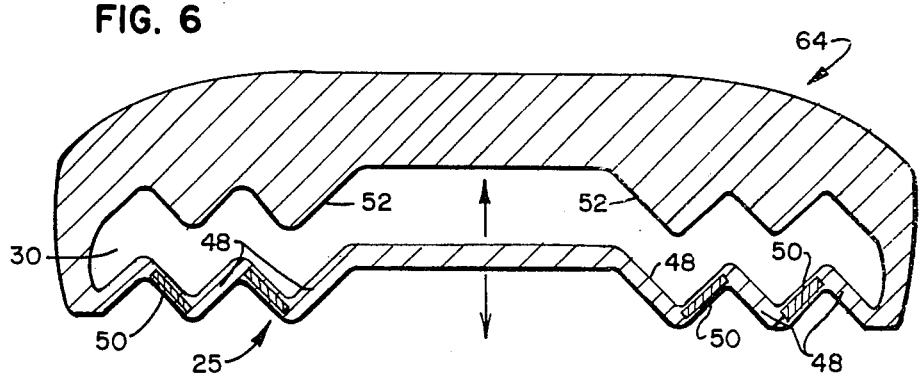
FIG. 6 is a sectional view of an infusion pump, operational elements thereof not being shown for purposes of illustration, illustrating a top inside surface thereof configured in accordance with the principles of the present invention to enable nesting of the flexible spring diaphragm thereagainst when the drug chamber is empty.

The spring diaphragm 25 forms the flexible bottom wall portion 26 of the drug chamber 30 as generally shown in FIG. 2. The outside surface of the flexible spring diaphragm 25 is exposed to the body and senses internal body pressure so as to compensate for changes in the internal body pressure caused by changes in atmospheric pressure and temperature. The flexible spring diaphragm 25 communicates the internal body pressure to the drug chamber 30. In the embodiment shown in FIG. 2, and as illustrated in FIG. 6, an inner surface 52 of the top wall portion 24 is preferably configured, i.e., has a somewhat convoluted shape, so as to allow the spring diaphragm 25 to nest into the complimentary shape of the inner surface 52. This enables the spring diaphragm 25 to expel substantially all of the drug solution from the drug chamber 30 prior to refilling of the drug chamber 30. Moreover, the inner surface 52, just as with the spring diaphragm 25, might include a nested series of conical sections interconnected by a substantially stiff cylindrical ring in order to provide a spring diaphragm complementary to that of the spring diaphragm 25. It will be appreciated, that in this embodiment, the spring diaphragm 25 of the bottom wall portion 26 will provide most of the flexing action.

The spring diaphragm 25 is extended beyond its nested position when assembled such that the spring diaphragm 25 is therefore under stress. The initial displacement is selected to bring the pressure or force exerted by the spring diaphragm 25 to the flat portion of the force/displacement curve illustrated in FIG. 3. The functional volume of the infusion pump 20 is that displacement which takes place over this substantially flat region of the force/deflection curve. To limit the filling of the infusion pump to this displacement of the spring diaphragm 25, a telescoping section 54 is interconnected to the spring diaphragm 25 and extends into the inlet conduit 32. When the telescoping section 54 is fully extended, collar portion 56 cooperates with a collar portion 58 of the inlet conduit 32 to prevent the spring diaphragm 25 from traveling more than the desired distance. As illustrated, the telescoping section 54 is interconnected to a substantially flat portion 60 of the spring diaphragm. The telescoping section 54, thus limits the stroke of the spring diaphragm 25 as indicated generally by the arrows 62 and causes the filling back pressure to increase rapidly, thereby, reducing the risk of damaging the spring diaphragm 25 or causing errors in a drug flow rate due to excess pressure in the drug chamber.

It will be appreciated that the drug infusion site must be considered in the design of the infusion pump. For example, if the catheter must deliver the drug into the relatively high pressure of the arterial system, the pump pressure will need to be larger to maintain the same error limits that can be obtained when delivering the drug intravenously or intraperitoneally.

Moreover, although a preferred embodiment of the present invention has been described above, it will be appreciated that other pressure compensating means in accordance with the principles of the present invention might be utilized. In particular, other constant force spring arrangements might be utilized as a pressure source.

It is to be understood that even though the above numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention to the full extent indicated by the broad general meaning of the terms in which the appended claims are expressed.

What is claimed is:

1. An infusion pump for implantation in a living body, comprising:
   (a) a housing having a variable volume drug chamber;
   (b) spring energy source means being the principle force means for forcing drug solution out of the drug chamber into the body and compensating for changes in internal body pressure whereby pressure differential between the drug chamber and internal body pressure remains constant despite changes in body temperature or atmospheric pressure;

(c) an inlet conduit located at a first position on the housing in communication with the drug chamber;

(d) an outlet conduit located in a second position on the housing in communication with the drug chamber and leading to an infusion site in the living body, the outlet conduit including flow resistance means for resisting drug solution flow and means for delivery of the drug to the desired site; and (e) a self-sealing penetrable member positioned in the inlet conduit, the self-sealing penetrable member being unobstructed so that the infusion pump can be implanted in the body with the unobstructed self-sealing penetrable member situated adjacent a surface area of the body whereby the drug chamber can be refilled with drug solution periodically by injection through the skin.

2. An infusion pump in accordance with claim 1, wherein the spring energy source means includes spring means for exerting a predetermined substantially constant force over a predetermined range of movement.

3. An infusion pump in accordance with claim 2, wherein the spring means includes spring diaphragm means for forming a movable external wall portion of the housing.

4. An infusion pump in accordance with claim 3, wherein the spring diaphragm means includes a conical spring member.

5. An infusion pump in accordance with claim 3, wherein the spring diaphragm means includes a plurality of conical spring sections interconnected by more stiff ring sections forming a spring diaphragm member.

6. An infusion pump in accordance with claim 3, wherein the spring diaphragm means includes a plurality of conical spring sections alternated radially with stronger conical sections reversely oriented.

7. An infusion pump for implantation in a living body; comprising:

(a) a housing having a strong external shell structure;

(b) movable spring diaphragm means forming a portion of the external shell structure and cooperating with the remainder of the shell structure for providing a variable volume, drug chamber for holding a drug solution, the spring diaphragm means being acted on and being responsive to internal body pressure so as to provide a substantially uniform pressure differential between the drug chamber and the internal body pressure, the movable spring diaphragm means being the principal force means for forcing the drug solution from the drug chamber into the body; and (c) means for delivering the drug solution to the body from the drug chamber.

8. An infusion pump in accordance with claim 7, wherein the spring diaphragm means exerts a substantially constant force over a predetermined range of movement.

9. An infusion pump in accordance with claim 8, wherein the infusion pump includes means for limiting movement of the spring diaphragm means whereby the spring diaphragm means is limited to a range of movements wherein the spring diaphragm means exerts a substantially constant force.

10. An infusion pump in accordance with claim 8, wherein the spring diaphragm means includes a plurality of conical spring sections radially spaced apart and interconnected by relatively stiff sections having a higher elastic constant than the conical spring sections.

11. An infusion pump in accordance with claim 10, wherein the spring diaphragm means exerts a force of 4 to 15 psi on the drug solution in the drug chamber.

12. An infusion pump in accordance with claim 10, wherein the spring diaphragm means is moveable between a first position and a second position, the spring diaphragm means being stressed at both positions so as to exert a substantially constant force over its range of movement between the first and second positions.

13. An infusion pump for implantation in a living body, comprising:

(a) a housing defining a variable volume, fluid tight drug chamber;

(b) moveable spring diaphragm means forming a wall portion of the drug chamber for exerting a force on the drug solution in the drug chamber, the spring means further forming an exterior wall portion of the housing and being subjected to a force exerted by internal body pressure, whereby changes in body pressure cause corresponding changes in the amount of force applied by the spring diaphragm means on the drug solution in the drug chamber, the spring diaphragm means including plurality of conical sections radially spaced apart and interconnected by sections having a higher elastic constant so as to provide a substantially constant force over a predetermined range of movement;

(c) inlet conduit means for providing fluid communication between the drug chamber and an exterior of the housing;

(d) outlet conduit means for providing fluid communication between the drug chamber and an infusion site in the body; and (e) a self-sealing, penetrable member in the inlet conduit means, the self-sealing, penetrable member being unobstructed so that the pump can be implanted in the body with the unobstructed penetrable member situated adjacent a surface area of the body whereby the drug chamber can be refilled with drug solution periodically by injection through the skin.

14. The method of infusing liquids into a living body, a method comprising:

(a) implanting a self-powered pump including spring diaphragm means into a living body, with an inlet conduit leading to a drug chamber of the pump;

(b) interconnecting an outlet conduit to at least one infusion site in the body;

(c) injecting drug solution through skin of the body and through a self-sealing, penetrable member positioned in the inlet conduit to fill the drug chamber; and (d) exerting a force on the drug solution in the drug chamber corresponding to the cumulative total force of the spring diaphragm means and the internal body pressure whereby pressure differential between the drug chamber and the internal body pressure is maintained relatively constant, the force being exerted by the spring diaphragm means being the principal force for forcing the drug solution out of the drug chamber into the body.

15. An infusion pump in accordance with claim 13, wherein the spring diaphragm means is the principal force means for forcing the drug solution out of the drug chamber.

* * * * *

UNITED STATES PATENT AND TRADEMARK OFFICE
CERTIFICATE OF CORRECTION

PATENT NO. : 4,772,263

DATED : September 20, 1988

INVENTOR(S) : Dorman et al.

It is certified that error appears in the above-identified patent and that said Letters Patent is hereby corrected as shown below:

Column 3, Line 22, "linerally" should be --linearally--.

Column 5, Line 62, "penetratable" should be --penetrable--.

Column 6, Line 13, "Poisseuille" should be --Poiseuille--.

Column 6, Line 14, delete first occurrence of "r".

Column 7, Line 50, "Xydor®" should be --Xydar®--.

Column 8, Line 63, "principle" should be --principal--.

Signed and Sealed this

Twenty-eighth Day of March, 1989

Attest:

DONALD J. QUIGG

*Attesting Officer*  Commissioner of Patents and Trademarks